United States Patent
Fukunaka et al.

(10) Patent No.: US 6,476,262 B2
(45) Date of Patent: Nov. 5, 2002

(54) UREA SYNTHESIS PROCESS AND APPARATUS

(75) Inventors: Tadashi Fukunaka, Chiba (JP); Kenji Yoshimoto, Chiba (JP); Kenji Sakai, Chiba (JP); Yasuhiko Kojima, Chiba (JP)

(73) Assignees: Toyo Engineering Corporation, Tokyo (JP); PT Pupuk Sriwidjaja, Palembang (ID)

( * ) Notice: Subject to any disclaimer, the term of this patent is extended or adjusted under 35 U.S.C. 154(b) by 0 days.

(21) Appl. No.: 09/897,967

(22) Filed: Jul. 5, 2001

(65) Prior Publication Data

US 2002/0004612 A1 Jan. 10, 2002

(30) Foreign Application Priority Data

Jul. 4, 2000 (JP) ........................................ 2000-202482

(51) Int. Cl.[7] ............................................. C07C 273/00
(52) U.S. Cl. .............................. 564/67; 564/68; 564/70; 564/71; 564/72
(58) Field of Search ............................. 564/67, 68, 70, 564/71, 72

(56) References Cited

U.S. PATENT DOCUMENTS 4,420,635 A * 12/1983 Washington et al. ........ 562/555
5,936,122 A * 8/1999 Kjima et al. .................. 564/67

* cited by examiner

Primary Examiner—Jafar Parsa
(74) Attorney, Agent, or Firm—Oblon, Spivak, McClelland, Maier & Neustadt, P.C.

(57) ABSTRACT

Urea is prepared by reacting ammonia and carbon dioxide in an apparatus comprising a vertical condensation and synthesis column and a stripper, to provide a urea synthesis solution comprising urea, unreacted ammonia, unreacted carbon dioxide and water. The urea synthesis solution is transferred from the top of the vertical condensation and synthesis column to the top of a stripper. Carbon dioxide is introduced into the bottom of the stripper and contacted with the urea synthesis solution, thereby separating the unreacted ammonia and the unreacted carbon dioxide from the urea, and providing a mixed gas comprising ammonia, carbon dioxide and water. The mixed gas is transferred into the bottom of the vertical condensation and synthesis column, where it is reacted with liquid ammonia injected into the bottom and a middle of the vertical condensation and synthesis column. The mixed gas and liquid ammonia are condensed and react to form urea, Uncondensed gases are absorbed in an absorbing medium, which is subsequently recycled to the bottom of the vertical condensation and synthesis column.

16 Claims, 5 Drawing Sheets

UREA SYNTHESIS PROCESS AND APPARATUS

BACKGROUND OF THE INVENTION

1. Field of the Invention

The present invention relates to a urea synthesis method comprising separating unreacted ammonia and unreacted carbon dioxide from the reaction mixture by stripping the mixture with the entire carbon dioxide feedstock, at a pressure substantially equal to the urea synthesis pressure.

2. Description of the Related Art

Methods for preparing urea in which ammonia is reacted with carbon dioxide, are well known, and a variety of proposals have been made for urea synthesis methods. For example, ammonia may be reacted with carbon dioxide in a urea synthesis zone at a desired urea synthesis pressure and urea synthesis temperature, and the unreacted ammonium carbamate may then be separated from the product urea synthesis solution as a mixed gas of ammonia and carbon dioxide. This mixed gas may then be absorbed in an absorbing medium and recirculated to the urea synthesis zone, thereby providing a urea solution from which the ammonium carbamate has been separated from the urea synthesis solution.

Generally, a urea plant consists of a synthesis column, a carbamate condenser and a stripper. Often, the bottoms of the synthesis column and the carbamate condenser are placed at a height of 20 to 30 meters above the ground. In this case, the supporting structure is composed of concrete was laid up to this height, or a combination of concrete with a steel framed structure was built, rather than solely a steel-frame structure. In light of the time and effort required for the installation and maintenance of such apparati, urea synthesis processes with urea synthesis columns and the like placed on the ground have been developed.

The present inventors have previously proposed (Japanese Patent Laid-Open No. 10-182587) an improved method of synthesizing urea, comprising stripping unreacted ammonia and carbon dioxide from the product mixture with the carbon dioxide feedstock. This method allows the equipment to be placed on the ground, rather than elevated as described above. This method comprises providing a vertical condenser above the urea synthesis column so that the mixed gas from the stripper contacts the absorbing medium under cooled conditions, in order to condense the mixed gas. The apparatus in which this method is practiced has a first down-flow-pipe passing from the top of the condenser to the bottom of the synthesis column in order to allow the resulting condensate to flow down to the bottom of the synthesis column by means of gravity. This condensate liquid, along with a part of the liquid ammonia or carbon dioxide starting materials participate in the synthesis of urea. The urea synthesis solution, provided by means of a second down-flow-pipe having an opening in the top of the synthesis column, is introduced into the stripper by means of gravity. The unreacted ammonia and carbon dioxide, i.e., the above-described mixed gas, is separated with the remainder of the carbon dioxide starting material and introduced into the bottom of the above-described condenser and a condensed, or the condensate liquid is sucked from the vertical condenser into the bottom of the urea synthesis by means of an ejector using preheated liquid ammonia starting material as a driving fluid to promote the synthesis of urea from the condensate.

However, in the above-described method, the ammonia and carbon dioxide separated at the top of the condenser are absorbed by the absorbing medium in the scrubber, without being recycled to the bottom of the urea synthesis column, and thus do not add heat to the urea synthesis column (i.e., because the heat of formation of ammonium carbamate due to the reaction between ammonia and carbon dioxide is not generated in the urea synthesis column). Thus, it is desirable to produce ammonium carbamate in the urea synthesis column by introducing a portion of the carbon dioxide feedstock into the urea synthesis column, in order to raise its temperature by means of the heat of the reaction.

Stamicarbon B.V. has also proposed a method in which the synthesis of urea and absorption of uncondensed gas is performed in one horizontal apparatus using a horizontal condenser combined with a horizontal urea synthesis reactor. The mixed gas containing ammonia and carbon dioxide from the stripper may be condensed to produce ammonium carbamate, in order to recover the heat formed at this time.

However, in this method, since the liquid flows only in the horizontal direction and the gas flows only upward, the liquid-gas contact is insufficient and the condensation rate of the gas remains low. Also, an almost ideal plug flow cannot be obtained, and therefore the rate of urea synthesis is low, thereby increasing the required capacity of this horizontal apparatus per unit production. Also, a large surface area is required for installing a horizontal apparatus. Furthermore, in order for the gas to flow uniformly in a horizontally oriented apparatus, a gas dispersion unit with a large pressure loss is required. There are also various additional problems, such as the large space required for liquid-gas separation.

SUMMARY OF THE INVENTION

One object of the present invention is to provide a urea synthesis process in which a mixed gas of unreacted ammonia and carbon dioxide has sufficient contact with a liquid phase, the required capacity of an apparatus employing this method, per unit production, is small, and condensation of the mixed gas and synthesis of urea are unified. This is provided by reacting ammonia and carbon dioxide in a vertical condensation and synthesis zone, stripping the resulting urea synthesis solution with the carbon dioxide feedstock in a stripping zone, and recycling the unreacted carbon dioxide and ammonia obtained by stripping the urea synthesis solution back to the vertical condensation and synthesis zone.

A second object of the present invention is to provide a urea synthesis apparatus for carrying out the above described process.

Other objects of the present invention will be apparent from the following descriptions.

The above described objects of the present invention are achieved by the urea synthesis process and apparatus described below.

DETAILED DESCRIPTION OF THE INVENTION

A first embodiment of the present invention is a urea synthesis process in which ammonia is reacted with carbon dioxide in a vertical condensation and synthesis zone at a temperature and pressure sufficient to provide a urea synthesis solution comprising urea, unreacted ammonia, unreacted carbon dioxide and water. The urea synthesis solution is then contacted with the carbon dioxide feedstock in a heated stripping zone at a pressure substantially equal to the urea synthesis pressure, thereby separating the unreacted ammonia and the unreacted carbon dioxide as a mixed gas of ammonia, carbon dioxide and water. The urea synthesis solution, containing residual unreacted ammonia and unreacted carbon dioxide that were not separated in the stripping zone, is further processed to provide urea, while the mixed gas separated in the stripping zone is introduced into the condensation and synthesis zone and contacted with an absorbing medium and liquid ammonia and cooled to condense the mixed gas and carry out the synthesis of urea. The mixed gas and the absorbing medium are supplied to a bottom part of the vertical condensation and synthesis zone, the liquid ammonia feedstock is supplied to the bottom and middle part of the vertical condensation and synthesis zone, and the urea synthesis solution flows down, by means of gravity, from a top portion of the vertical condensation and synthesis zone to a top portion of the stripping zone.

The pressure at which the synthesis of urea is carried out in the vertical condensation and synthesis zone is preferably in the range of 13 to 25 MPaG (gauge pressure), including pressures of 14, 15, 16, 17, 18, 19, 20, 21, 23, and 24 MPaG, inclusive of all values and subranges therebetween. In the condensation portion of the condensation and synthesis zone, the temperature of the liquid is preferably kept at 165 to 190° C., including 170, 180, and 185° C. The mole ratio of ammonia to carbon dioxide (abbreviated as N/C) and the mole ratio of water to carbon dioxide (abbreviated as H/C) in the condensation portion of the condensation and synthesis column are preferably kept at 2.5 to 4.5, and 1.0 or smaller, respectively. The temperature of the liquid in the synthesis portion of the condensation and synthesis zone is preferably kept at 170 to 200° C., including 175, 180, 185, 190 and 195° C., inclusive of all values and subranges therebetween. The N/C and H/C ratios in the synthesis portion of the condensation and synthesis zone are preferably 3.5 to 5.0, and 1.0 or smaller, respectively.

In the vertical condensation and synthesis zone, a percent urea conversion of 20 to 75%, preferably 60 to 75%, may be achieved.

The pressure of the stripping zone is substantially equal to that of the condensation and synthesis zone, i.e., 13 to 25 MPaG (gauge pressure), including pressures of 14, 15, 16, 17, 18, 19, 20, 21, 22, 23, and 24 MPaG, inclusive of all values and subranges therebetween. The term "substantially equal" means that the pressures of the stripping zone and the vertical condensation and synthesis zone differ by 0.5 MPa or less. The temperature of the stripping zone is preferably kept at 160 to 200° C., including 165, 170, 175, 180, 185, 190, and 195° C., inclusive of all values and subranges therebetween. Preferably, in order to increase the rate of stripping, unreacted ammonia and carbon dioxide from the urea synthesis solution, the full amount of the carbon dioxide starting material is used for stripping A second embodiment of the present invention is a urea synthesis process in which ammonia is reacted with carbon dioxide in a vertical condensation and synthesis zone at a temperature and pressure sufficient to provide a urea synthesis solution comprising urea, unreacted ammonia, unreacted carbon dioxide and water. The urea synthesis solution is then contacted with the carbon dioxide feedstock in a heated stripping zone at a pressure equal to or slightly lower (i.e., at a pressure 0.05 to 5 MPa lower) than the urea synthesis pressure, thereby separating the unreacted ammonia and the unreacted carbon dioxide as a mixed gas of ammonia, carbon dioxide and water. The urea synthesis solution, containing residual unreacted ammonia and unreacted carbon dioxide that were not separated in the stripping zone, is further processed to provide urea, while the mixed gas separated in the stripping zone is increased in pressure 0.05 to 5 MPa and introduced into the bottom portion of the condensation and synthesis zone, contacted with an absorbing medium and liquid ammonia and cooled to condense the mixed gas and carry out the synthesis of urea. The absorbing medium is supplied to a bottom part of the vertical condensation and synthesis zone and the liquid ammonia feedstock is supplied to the bottom and middle part of the vertical condensation and synthesis zone.

The condensation and synthesis zone of the process of the second embodiment is maintained at a pressure, temperature, N/C and H/C ratio as described above for the process of the first embodiment of the present invention. However, in the process of the second embodiment, the stripping zone is operated at a pressure equal to or slightly lower (i.e., 0.05 to 5 MPa lower) than the pressure of the condensation and stripping zone. The temperature and N/C and H/C ratios of the process of the third embodiment are as described above for the process of the first embodiment.

A third embodiment of the present invention is a urea synthesis process in which ammonia is reacted with carbon dioxide in a vertical condensation and synthesis zone at a temperature and pressure sufficient to provide a urea synthesis solution comprising urea, unreacted ammonia, unreacted carbon dioxide and water. The urea synthesis solution is then contacted with carbon dioxide in a heated stripping zone at a pressure substantially equal to the urea synthesis pressure, thereby separating the unreacted ammonia and the unreacted carbon dioxide as a mixed gas of ammonia, carbon dioxide and water. The urea synthesis solution, containing residual unreacted ammonia and unreacted carbon dioxide that were not separated in the stripping zone, is further processed to provide urea, while the mixed gas separated in the stripping zone is increased in pressure 0.05 to 5 MPa and introduced into the bottom portion of the condensation and synthesis zone, contacted with an absorbing medium and liquid ammonia and cooled to condense the mixed gas and carry out the synthesis of urea. The mixed gas and the absorbing medium are supplied to a bottom part of the vertical condensation and synthesis zone, the liquid ammonia is supplied to the bottom and middle part of the vertical condensation and synthesis zone, and the urea synthesis solution is removed from a top portion of the condensation and synthesis zone and introduced to a top portion of the stripping zone.

The condensation and synthesis zone and stripping zone of the process of the third embodiment are maintained at a pressure, temperature, N/C and H/C ratio as described above for the process of the first embodiment of the present invention.

A fourth embodiment of the present invention is an apparatus comprising (a) a vertical condensation and synthesis column having a cooler in a portion extending from a bottom portion (i.e., the bottom portion is approximately the lower third of the condensation and synthesis column, preferably the lower 20% of the column) to a middle portion (i.e., the middle portion is approximately the central third of the condensation and synthesis column, preferable the central 20% of the column), (b) a stripper for separating a mixed gas of unreacted ammonia, unreacted carbon dioxide and water from a urea synthesis solution by stripping the urea synthesis solution with carbon dioxide, (c) a pipe for supplying liquid ammonia to the bottom portion and middle portion of the vertical condensation and synthesis column, (d) a pipe that has an opening at one end thereof in a top portion of the vertical condensation and synthesis column (i.e., the top portion is approximately the top third of the condensation and synthesis column, preferably the top 20% of the column) connected to a top portion of the stripper (i.e., similarly, the top portion of the stripper is approximately the top third of the stripper, preferably the top 10% of the stripper), for introducing the urea synthesis solution into a top portion of the stripper by means of gravity, (e) a pipe connected to the bottom portion of the vertical condensation and synthesis column for introducing the mixed gas from the stripper to the vertical condensation and synthesis column, (f) a scrubber provided in the top portion of the vertical condensation and synthesis column for absorbing, with an absorbing medium, the ammonia and carbon dioxide from an inert gas separated from the urea synthesis solution in the vertical condensation and synthesis column, (g) a pipe for discharging the inert gas from the top portion of the scrubber, (h) a pipe for introducing into the bottom portion of the vertical condensation and synthesis column the absorbing medium containing absorbed ammonia and carbon dioxide from the scrubber, (i) a pipe for introducing carbon dioxide into the bottom portion of the stripper, and (j) a pipe for discharging an aqueous urea solution containing residual unreacted ammonia and unreacted carbon dioxide that are not separated from the aqueous urea solution from the bottom portion of the stripper (i.e, the bottom portion of the stripper is approximately the bottom third of the stripper, preferably the bottom 10% of the stripper).

In the apparatus of the fourth embodiment of the present invention, a portion of the ammonia feedstock, the absorbing medium and the mixed gas from the stripper are introduced into the bottom portion of the vertical condensation and synthesis column, and the remainder of the liquid ammonia feedstock is introduced in the middle portion the condensation and synthesis column. A collection of U-pipes are provided for the portion of the vertical condensation and synthesis column extending from the bottom of the column to the middle portion thereof, and water, for example, flows through this collection of U-pipes to cool the lower portion of the condensation and synthesis column. This portion of the condensation and synthesis column is a condensing portion which functions similarly to the condenser in a conventional urea synthesis apparatus.

The portion above the middle portion of the vertical condensation and synthesis column (i.e., the portion above the condensation portion of the column) is the synthesis portion of the column, and performs the function of a urea synthesis column. Condensed liquid containing ammonium carbamate, produced in the condensation portion of the column, rises to the synthesis portion, along with a small amount of uncondensed gas. Liquid ammonia is supplied to the synthesis portion, and is reacted with the carbon dioxide in the uncondensed gas to produce the ammonium carbamate.

The top part of the synthesis portion is provided with an opening for a pipe to deliver the urea synthesis solution produced in the synthesis portion of the column to the top part of the stripper. The portion above the liquid surface of the top part of the synthesis portion is a liquid-gas separation portion for separating the uncondensed gas from the urea synthesis solution. A scrubbing portion is provided above the liquid-gas separation portion to wash and absorb separated gas with the absorbing medium. The absorbing medium is a liquid which contains ammonium carbamate obtained by the reaction of previously unreacted ammonia and carbon dioxide contained in the urea solution discharged from the stripper, and an ammonium carbamate solution that is obtained by collecting ammonia and carbon dioxide discharged along with an inert gas from an absorbing portion.

The absorbing medium that has absorbed ammonia and carbon dioxide in the scrubbing portion is allowed to flow down through the pipe into the bottom part of the vertical condensation and synthesis column.

The ratios of volumes of the condensing portion of the column, the synthesis portion of the column, and the separation portion and scrubbing portion of the column to the whole volume of the vertical condensation and synthesis column are preferably in the range of 40 to 50%, 40 to 50%, 3.0 to 7.0% and 1.0 to 5.0%, respectively. Preferably, 1.0 to 50.0% of liquid ammonia is introduced into the middle part of the vertical condensation and synthesis column.

As discussed above, when the processes of the present invention are carried out in the apparatus of the fourth embodiment of the present invention, the pressure of the vertical condensation and synthesis column is preferably in the range of 13 to 25 MPaG (and values and subranges therebetween, as discussed above). Likewise, the temperature, N/C and H/C of the liquid in the condensation portion of the column are preferably maintained at 165 to 190° C., 2.5 to 4.5 and 1.0 or smaller, respectively (and values and subranges therebetween, as discussed above). The temperature, the N/C and the H/C of the liquid in the synthesis portion of the column are preferably maintained at 170 to 200° C., 3.5 to 5.0 and 1.0 or smaller, respectively (and values and subranges therebetween, as discussed above).

In the vertical condensation and synthesis column of the present invention, urea yields of up to 60 to 75% may be achieved.

It is preferable that in the vertical condensation and synthesis column, at least the condensation portion is provided with a baffle plate to improve liquid-gas contact.

Stripping is performed while the pressure of the stripper is kept at a pressure substantially equal to or slightly lower than the urea synthesis pressure (depending upon the process conditions employed) and the temperature of the stripper is preferably kept at 160 to 200° C. The full amount of carbon dioxide is preferably used for stripping in order to increase the rates of stripping of unreacted ammonia and carbon dioxide from the urea synthesis solution.

In the apparatus of the fourth embodiment, the urea synthesis solution obtained from the top of the vertical condensation and synthesis column is allowed to flow down to the top of the stripper by means of gravity.

A fifth embodiment of the present invention is an apparatus comprising (a) a vertical condensation and synthesis column placed on the ground, having a cooler in a portion extending from a bottom portion to a middle portion thereof, (b) a stripper placed at substantially the same level, (i.e., the vertical elevation of the bottom of the stripper and the column differ by no more than 1 meter, e.g., placed on the ground) for separating a mixed gas of unreacted ammonia, unreacted carbon dioxide and water from a urea synthesis solution by stripping the urea synthesis solution with carbon dioxide, (c) a pipe for supplying liquid ammonia to the bottom portion and middle portion of the vertical condensation and synthesis column, (d) a pipe comprising pressure raising means (for example, a pump or compressor located approximately in the middle portion of the pipe), which has an opening in an end thereof in a top portion of the vertical condensation and synthesis column for introducing the urea synthesis solution into a top portion of the stripper, (e) a pipe for introducing into the bottom portion of the vertical condensation and synthesis column the mixed gas from the stripper, (f) a scrubber that is provided in the top portion of the vertical condensation and synthesis column for absorbing, with an absorbing medium, ammonia and carbon dioxide in an inert gas separated from the urea synthesis solution in the vertical condensation and synthesis column, (g) a pipe for discharging the inert gas from a top portion of the scrubber, (h) a pipe for introducing the absorbing medium containing absorbed ammonia and carbon dioxide from the scrubber into the bottom portion of the vertical condensation and synthesis column, (i) a pipe for introducing carbon dioxide into a bottom portion of the stripper, and (j) a pipe for discharging an aqueous urea solution containing residual unreacted ammonia and unreacted carbon dioxide that are not separated from the aqueous urea solution, from the bottom portion of the stripper.

The apparatus of the fifth embodiment may be operated similarly to the apparatus of the fourth embodiment, using the pressure temperature, N/C, and H/C ratios as described above. However, in the fifth embodiment, the pipe (d) is provided with pressure raising means (i.e., a compressor or pump) which raises the pressure of the urea synthesis solution introduced into the top part of the stripper by 0.05 to 0.5 MPa.

A sixth embodiment of the present invention is an apparatus comprising (a) a vertical condensation and synthesis column placed on the ground, having a cooler in a portion extending from a bottom portion to a middle portion, (b) a stripper placed at substantially the same level for separating a mixed gas of unreacted ammonia, unreacted carbon dioxide and water from a urea synthesis solution by stripping the urea synthesis solution with the carbon dioxide feedstock, (c) a pipe that has an opening in one end in a top portion of the vertical condensation and synthesis column, connected to the stripper, for introducing a urea synthesis solution into the top portion of the stripper, (d) a pipe for supplying liquid ammonia feedstock to the bottom portion and the middle portion of the vertical condensation and synthesis column, (e) a pipe comprising pressure raising means (for example, in the middle portion of the pipe), for introducing the mixed gas from the stripper into the bottom portion of the vertical condensation and synthesis column, (f) a scrubber that is provided in the top portion of the vertical condensation and synthesis column for absorbing, with an absorbing medium, the ammonia and carbon dioxide in the inert gas separated from the urea synthesis solution in the vertical condensation and synthesis column, (g) a pipe for discharging the inert gas from a top portion of the scrubber, (h) a pipe for introducing the absorbing medium from the scrubber containing absorbed ammonia and carbon dioxide into the bottom portion of the vertical condensation and synthesis column, (i) a pipe for introducing the carbon dioxide feedstock into a bottom portion of the stripper, and (j) a pipe for discharging an aqueous urea solution containing residual unreacted ammonia and unreacted carbon dioxide that are not separated from the aqueous urea solution from the bottom portion of the stripper.

The apparatus of the sixth embodiment may be operated similarly to the apparati of the fourth and fifth embodiments, using the pressure temperature, N/C, and H/C ratios as described above. However, in the sixth embodiment a pipe (e) is provided with pressure raising means (e.g., a blower) to raise the pressure of the mixed gas from the stripper, which is introduced in the bottom portion of the vertical condensation and synthesis column, by 0.05 to 5 MPa.

In the processes and apparati of present invention, it is not necessary to supply part of the carbon dioxide feedstock to the synthesis column in order to maintain the temperature of the synthesis column by means of the heat of reaction of carbon dioxide with ammonia, because a part of the liquid ammonia feedstock, a mixed gas of ammonia and carbon dioxide from the stripper, and the absorbing medium are supplied to the bottom part of the vertical condensation and synthesis column. Thus, an amount of ammonia and carbon dioxide equivalent to the amount discharged from the top of the condenser are effectively added to the vertical condensation and synthesis column as in cases where the condenser is separated from the synthesis column. Since the full amount of the carbon dioxide feedstock can be used for stripping, the rate of stripping is increased, and the recovery rate required in the down stream part of the process is reduced.

Also, by using a vertical condensation and synthesis column, the capacity coefficient of the liquid phase ($K_L a$, the rate at which the gas is dissolved in the liquid) is twice as large as the case in which a horizontal condensation and synthesis column is used, and thus the rate of urea synthesis is increased. In addition, the burden on the stripper is reduced.

Figure 1:
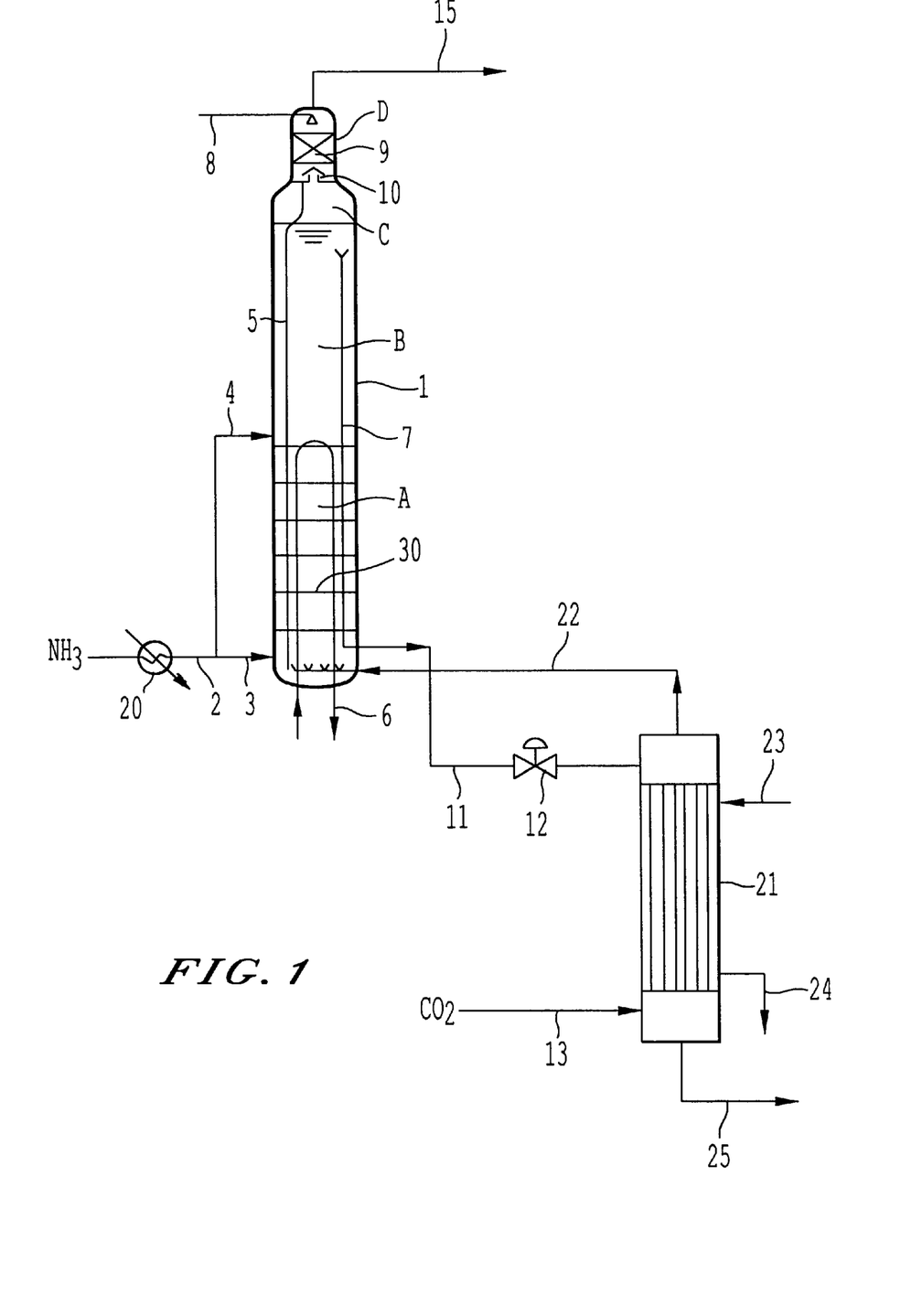
FIG. 1 is a diagram illustrating a first embodiment of the present invention.

The present invention will be further described below, referring to the FIGS. FIG. 1 is a diagram which illustrates the fourth embodiment of the present invention. In FIG. 1, the liquid ammonia feedstock is supplied from a pipe 2 to the bottom portion and the middle portion of a vertical condensation and synthesis column 1 through pipes 3 and 4, respectively. A gas mixture comprising ammonia, carbon dioxide and water which is separated in a stripper 21 and an absorbing medium that will be described later are introduced into the bottom portion of the vertical condensation and synthesis column 1 through pipe 22 and pipe 5, respectively.

The condensation portion A (the portion extending from the bottom to the middle portion) of the vertical condensation and synthesis column 1 is provided with cooling pipes 6. The cooling pipes preferably comprise a collection of inverse U-pipes. Water (or any other suitable heat exchange medium) is passed through the cooling pipes as a coolant, and the heat of formation from ammonium carbamate produced in a cooling portion A can be collected by converting the water in the U-pipes to steam. The ammonium carbamate produced therein rises through the condensation portion A into a synthesis portion B (the portion extending from the middle portion to the liquid surface of the top portion) of the vertical condensation and synthesis column 1, along with uncondensed ammonia and carbon dioxide. The operating conditions in the condensing portion A, i.e., the pressure, the N/C, the H/C, the temperature and the residence time are preferably 13 to 25 MPaG, 2.5 to 4.5, 1.0 or smaller, 165 to 190° C. and 10 to 30 minutes, respectively: Under these conditions, a urea yield of 20 to 60% may be achieved. The condensation rate will decrease and the temperature at which the ammonium carbamate is solidified will increase due to an increase in the partial pressure of carbon dioxide in the ammonium carbamate solution if the N/C is smaller than 2.5, and the rate of condensation will decrease due to a rise in the vapor pressure of ammonia if the N/C is greater than 4.5. Therefore, N/C is preferably 2.5 to 4.5. Also, if the H/C is greater than 1.0, the rate of urea synthesis at equilibrium will decrease. Accordingly, the H/C is preferably 1.0 or smaller. If the residence time is shorter than 10 minutes, the vapor pressure will rise and the rate of condensation will decrease due to a drop in the rate of urea synthesis. If the residence time is longer than thirty minutes, no significant increase in the rate of urea synthesis may be expected, thereby requiring an extreme increase in the capacity required in the condensing portion A. Thus, the residence time is preferably 10 to 30 minutes. The rate of urea synthesis decreases if the operation temperature is significantly lower than 170° C., and if the operation temperature is significantly higher than 190° C. the rate of condensation decreases and the corrosion of the materials of apparatus may increase due to a rise in vapor pressure. Accordingly, the operating temperature is preferably 170 to 190° C.

The condensed liquid introduced in the synthesis portion B from the condensation portion A of the vertical condensation and synthesis column 1 is mixed with the liquid ammonia feedstock introduced through pipe 4, thereby producing ammonium carbamate from the uncondensed ammonia and carbon dioxide. The heat of formation of the ammonium carbamate is used to provide the heat of reaction for the endothermic reaction through which ammonium carbamate is converted to urea. Furthermore, the temperature, the N/C, the H/C and residence time in the synthesis portion B are preferably 180 to 200° C., 3.5 to 5.0, 1.0 or smaller and 10 to 40 minutes, respectively, which provides a urea yield of 60 to 75%. If the N/C is smaller than 3.5, the equilibrium rate of synthesis will decrease. If the N/C exceeds 5.0, the ammonia will be gasified, resulting in an increase in the vapor pressure. If the H/C is greater than 1.0, the rate of synthesis will decrease. If the residence time of the reactants in synthesis portion B is shorter than ten minutes, the maximum rate of synthesis cannot be achieved, and if the residence time is greater than forty minutes, the maximum rate of synthesis has already been attained and further increases in the rate of synthesis would not be expected.

In the top portion of the synthesis portion B of the vertical condensation and synthesis column 1, the upper end of pipe 7 is provided in the vertical condensation and synthesis column in order to allow the urea synthesis solution produced in the condensation and synthesis column to flow into a stripper 21. A liquid surface is formed above the opening of pipe 7. The portion above the liquid surface is a liquid-gas separation portion C, which performs the function of separating inert gases (hydrogen and nitrogen contained in the carbon dioxide as well as air introduced in order to prevent the corrosion of apparatus) and accompanying ammonia and carbon dioxide from the urea synthesis solution.

The topmost portion of the vertical condensation and synthesis column 1 is provided with a scrubbing portion D having the function of washing the gas separated in the liquid-gas separation portion C by absorbing by the ammonia and carbon dioxide in the gas with an absorbing medium. The absorbing medium may be a liquid containing the ammonium carbamate obtained by collecting the unreacted ammonia and carbon dioxide in the urea solution from the stripper, which is introduced into the top part of the scrubbing portion D by a pipe 8, as described below. The introduced absorbing medium contacts the gas rising from the liquid-gas separation portion C in a packed bed 9, absorbs a part of ammonia and carbon dioxide therein, and flows down to the bottom of the vertical condensation and synthesis column 1 through pipe 5, which has an opening in a chimney portion 10. The pipe 5 is preferably provided inside the vertical condensation and synthesis column 1, but may also be provided outside the vertical condensation and synthesis column 1.

Figure 3A:
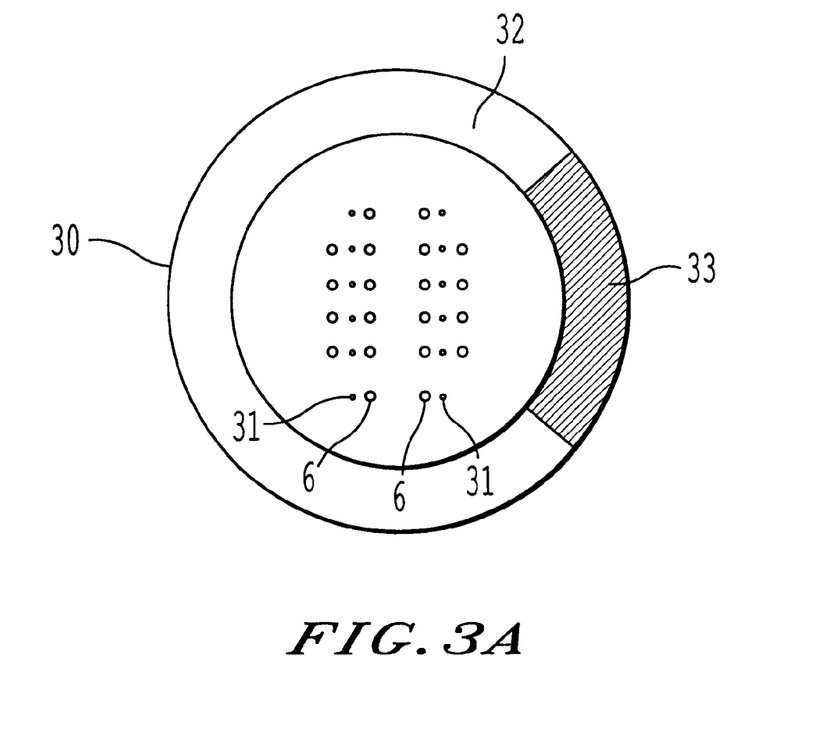
FIG. 3 is a diagram showing one example of a baffle plate for use in the present invention.
Figure 3B:
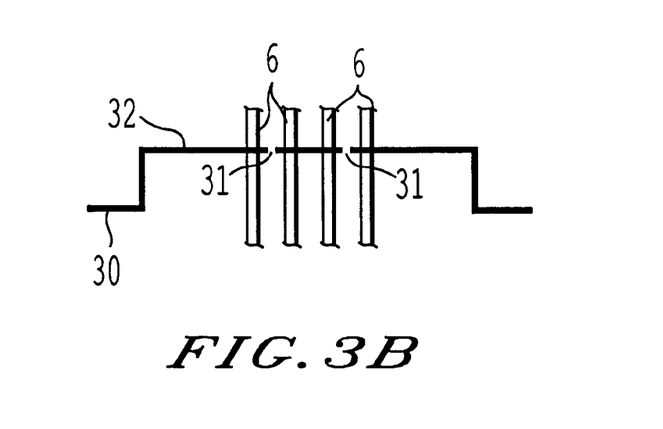

Preferably, at least the condensation portion A of the vertical condensation and synthesis column 1 may be provided with a baffle plate to improve liquid-gas contact. A variety of known baffle plates may be used. One example thereof is a type of baffle plate designed to make gases and liquids flow separately, as shown in FIG. 3. In FIG. 3, the gas flows upward through a plurality of holes 31 disposed between cooling pipes 6 and is cooled, while the liquid flows upward in a zigzag path (i.e., by "zigzag path" we mean a non-linear path) through a liquid passage 33 provided in the periphery of the baffle plate 30, in such a manner that the liquid intersects the flow of the gas. (The liquid passage of the upper or lower baffle plate is provided in a symmetrical position). Furthermore, an optional convex part 32 is preferably provided in the central part of the baffle plate in order to gather the gas in the plurality of small holes 31.

The unabsorbed gas containing ammonia and carbon dioxide that is discharged from a line in the top of the scrubbing portion D (FIG. 1) is washed by water in order to collect the ammonia and carbon dioxide.

The urea synthesis solution flowing down through pipe 7 from the top portion of the synthesis portion B of the vertical condensation and synthesis column 1 is introduced into the top portion of the stripper 21 by means of a pipe 11 and a controlling valve 12. The urea synthesis solution introduced through pipe 11 and valve 12 flows down through a heater in the stripper 21 (steam is introduced from a line 23 and condensate is discharged from a line 24) and contacts the carbon dioxide introduced into the bottom portion of the stripper 21 through pipe 13, thereby separating most of the unreacted ammonia and carbon dioxide from the urea synthesis solution. The separated mixture of unreacted ammonia and unreacted carbon dioxide, together with the carbon dioxide added through pipe 13, is supplied to the vertical condensation and synthesis column 1 through a pipe 22.

Particularly preferably, the operating pressure and the temperature of stripper 21, are 14 to 20 MPaG and 160 to 200° C., respectively. The total amount of carbon dioxide used in the synthesis of urea is preferably supplied to the stripper 21. Although not shown in FIG. 1, a portion of the carbon dioxide may be supplied to a low pressure decomposer for the remaining ammonium carbamate.

The liquid containing urea and the unreacted ammonia and carbon dioxide is withdrawn from the bottom part of the stripper, and transferred through pipe 25 to a low pressure decomposition step, and processed to provide urea. The unreacted ammonia and carbon dioxide are absorbed by water, dilute aqueous ammonia or the like, to provide a recovered solution. This recovered solution may be supplied as an absorbing medium to the scrubbing portion D of the vertical condensation and synthesis column 1, as described above.

Figure 2:
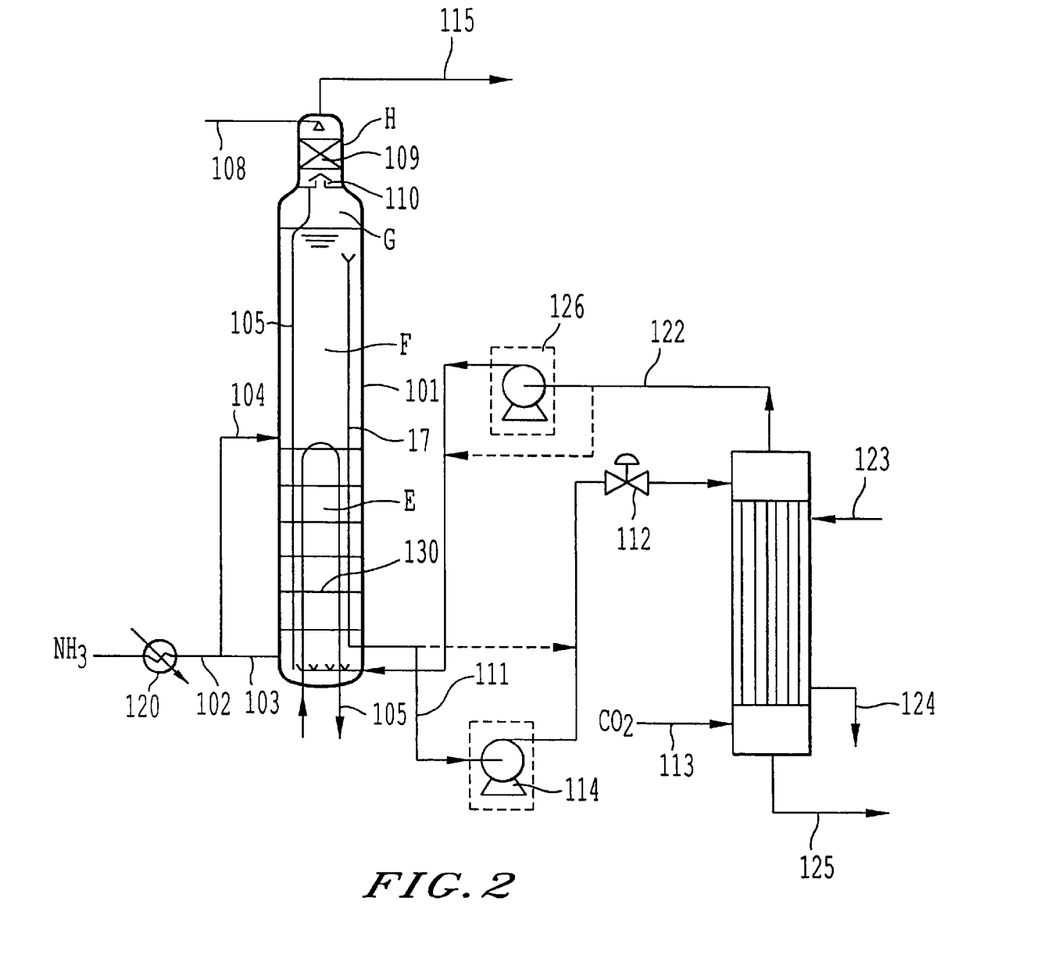
FIG. 2 is a diagram illustrating a second embodiment of the present invention, in which the bottom of a vertical condensation and synthesis column and the bottom of a stripper are both placed at substantially the same level (e.g., on the ground).

FIG. 2 is a diagram which illustrates another embodiment of the apparatus of the present invention, in which the bottom of both the vertical condensation and synthesis column 101 and stripper 121 are placed at substantially the same vertical elevation (e.g., on the ground). The apparatus described in FIG. 2 differs from that of FIG. 1 only in that a blower 126 for raising the pressure of the mixed gas by 0.05 to 5 MPa is provided at some point (e.g., the midpoint) in pipe 122 used to transfer the mixed gas from the stripper to the vertical condensation and synthesis column 101, or the line 111 for transferring the urea synthesis solution from vertical condensation and synthesis column 101 to the stripper is provided with a pump 114 for raising the pressure of the urea synthesis solution by 0.05 to 0.5 MPa. Furthermore, the blower 126 and the pump 114 are never used together. Thus, if the apparatus of FIG. 2 has the blower 126, it does not have the pump 114, and if the pump 114 is present, the apparatus of FIG. 2 does not have the blower 126.

Having generally described this invention, a further understanding can be obtained by reference to certain specific examples which are provided below for purposes of illustration only, and are not intended to be limiting unless otherwise specified.

EXAMPLE 1

An example of the production of 1725 tons of urea per day using the apparatus of FIG. 1 is presented below.

Liquid ammonia feedstock preheated to 75° C. by a pre-heater 20 was divided into two streams through pipe 2, so that 25.48 tons per day of liquid ammonia feedstock were introduced via pipe 3 into the bottom part of the vertical condensation and synthesis column 1, and 950.13 tons per day were introduced via pipe 4 into the middle part of the vertical condensation and synthesis column 1.

A mixed gas of 1608.32 tons per day of ammonia, 1637.91 tons per day of carbon dioxide and 150.57 tons per day of water from the top of the stripper 21 was introduced into the bottom part of the vertical condensation and synthesis column 1 via pipe 22. The recovered solution comprised 5.17 tons per day of urea. A mixture of 389.68 tons per day of ammonia, 482.63 tons per day of carbon dioxide and 320.42 tons of water, obtained from the stripper by separating and recovering the unreacted ammonia and carbon dioxide from the urea solution, was supplied to the top part of the scrubbing portion D via pipe 8, in order to absorb the ammonia and carbon dioxide from the uncondensed gas. The resulting absorbing liquid flowed down into the bottom of the vertical condensation and synthesis column 1 through pipe 5.

The vertical condensation and synthesis column 1 was maintained at a pressure of 15 MPa, and the temperature of the condensation portion A was maintained at 180° C. by cooling the condensation portion A with cooling pipes 6, thereby producing ammonium carbamate from ammonia and carbon dioxide. The condensed liquid containing ammonium carbamate flowed upward to the synthesis portion 8 along with the uncondensed ammonia and carbon dioxide, and the mixture was heated by the reaction of the liquid ammonia introduced via pipe 4, with the uncondensed ammonia and the uncondensed carbon dioxide, thereby providing urea. The residence time in the vertical condensation and synthesis column was forty minutes.

The urea synthesis solution product was introduced into the top part of the stripper 21 through pipes 7 and 11 and control valve 12. The remaining uncondensed ammonia and carbon dioxide was separated in the liquid-gas separation portion C. The composition of the urea synthesis solution comprised 1853.90 tons per day of urea, 1881.69 tons per day of ammonia, 744.74 tons per day of carbon dioxide, 1023.41 tons per day of water and 4.31 tons of biuret. 1211.59 tons of the carbon dioxide feedstock were supplied via pipe 13 to the stripper 21 and was contacted with the urea synthesis solution flowing down from the top part of the stripper at a pressure of 15 MPaG, at a temperature of 185° C., thereby removing the unreacted ammonia and carbon dioxide in the urea synthesis solution, to provide the aforesaid mixed gas.

The gas containing ammonia and carbon dioxide separated in the liquid-gas separation portion C was absorbed by the absorbing medium, comprising aqueous ammonium carbamate obtained by separating/recovering the unreacted ammonia and carbon dioxide in the urea solution from the stripper 21.

A gas containing 41.25 tons per day of ammonia, 17.34 tons per day of carbon dioxide and 3.68 tons per day of water was discharged from the top of the scrubbing portion D and was further treated to recover ammonia and carbon dioxide.

The urea solution containing 1764.23 tons per day of urea, 322.77 tons per day of ammonia, 381.63 tons per day of carbon dioxide, 846.97 tons of water and 7.24 tons of biuret was discharged from the bottom of the stripper 21. This urea solution was further treated to recover unreacted ammonia and carbon dioxide, and to concentrate the urea solution to provide 1725 tons per day of urea.

COMPARATIVE EXAMPLE 1

Figure 4:
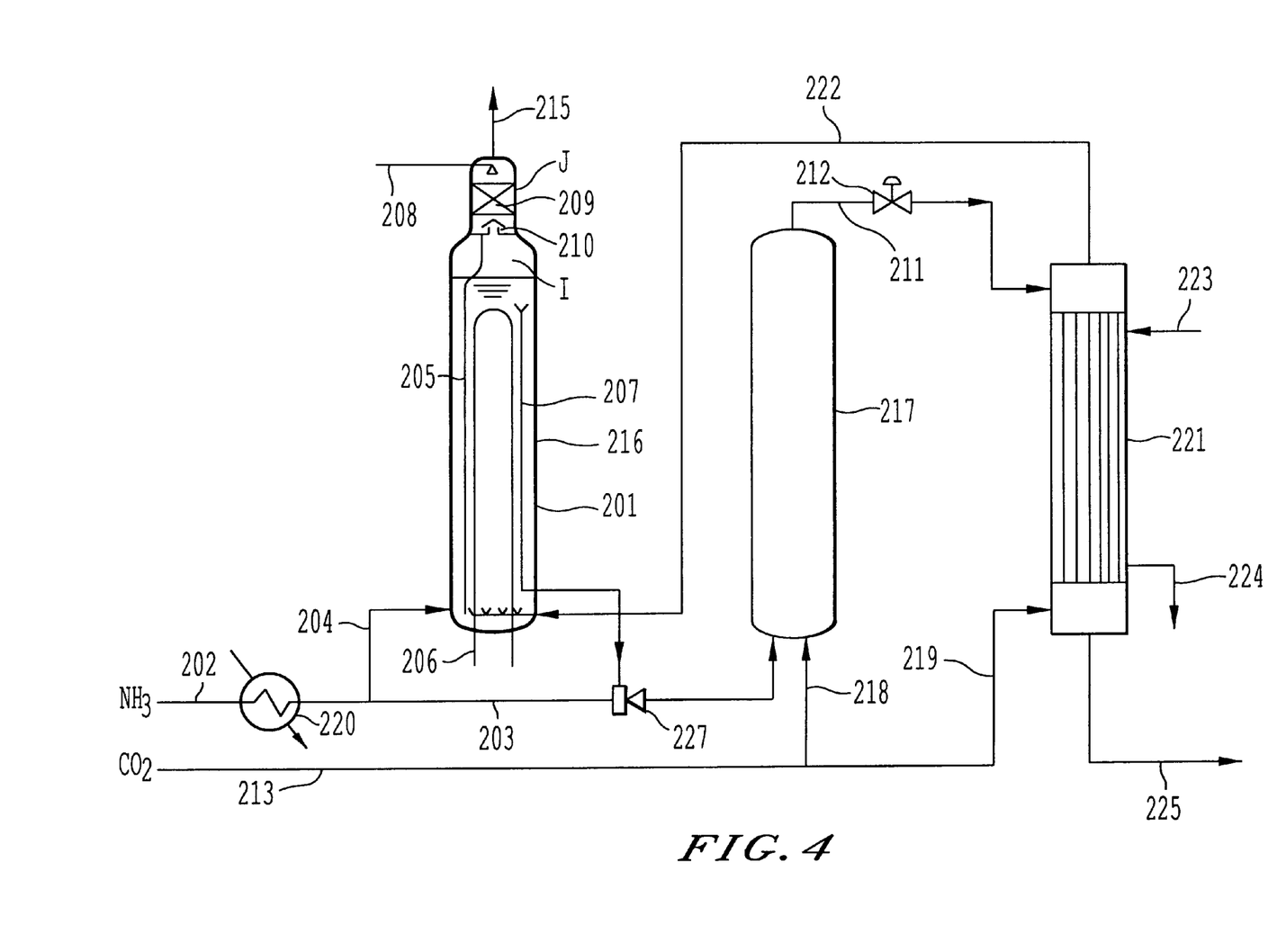
FIG. 4 is a diagram illustrating the process of Comparative Example 1.

An example of the production of 1725 tons of urea per day using an apparatus in which the condenser and synthesis column are separate is presented below for comparison with Example 1, referring to FIG. 4.

The condensate from the condenser 216 containing 1216.88 tons per day of urea, 1358.15 tons per day of ammonia feedstock, 1075.69 tons per day of carbon dioxide feedstock, 856.26 tons per day of water and 2.31 tons per day of biuret, in which the pressure was raised by an ejector 227 driven with 950.13 tons of liquid ammonia from pipe 203 preheated to 150° C., was supplied to a urea synthesis column 217 along with 171.36 tons per day of carbon dioxide via pipes 13 and 18. The reaction was carried out at a pressure of 15 MPaG and a temperature of 185° C., with a twenty minute residence time.

The urea synthesis solution containing 1853.88 tons per day of urea, 1945.86 tons per day of ammonia, 778.79 tons per day of carbon dioxide, 1047.95 tons per day of water and 4.31 tons per day of biuret was transferred from the top part of the synthesis column 217 to the stripper 221 via pipe 211 and control valve 212 and was contacted and heated with 1040.23 tons per day of carbon dioxide from pipe 219. Unreacted ammonia and carbon dioxide from the urea synthesis solution were separated as a mixed gas comprising 1598.58 tons per day of ammonia, 1469.46 tons per day of carbon dioxide and 154.63 tons per day of water.

A urea solution containing 1764.22 tons per day of urea, 396.69 tons per day of ammonia, 412.76 tons per day of carbon dioxide, 867.45 tons per day of water and 7.24 tons per day of biuret was removed from the bottom part of the stripper 221 through pipe 225, the ammonia and carbon dioxide contained therein were separated, and then the urea solution was concentrated to obtain 1725 tons per day of urea.

The aforesaid mixed gas from pipe 222 and 25.48 tons per day of liquid ammonia were supplied to the bottom of the condenser 216, and the recovered solution containing 5.75 tons per day of urea, 452.61 tons per day of ammonia, 545.43 tons per day of carbon dioxide and 341.28 tons per day of water, which came from separating/recovering unreacted ammonia and carbon dioxide was supplied via pipe 208 to the top of the scrubbing portion J in the top part of the condenser 216. After absorbing the uncondensed ammonia and carbon dioxide, the absorbing medium which came from the bottom part of the scrubbing portion J, was supplied to the bottom of the condenser 216 through the down-flow-pipe 205. The condenser 216 was cooled by means of cooling pipes 206 and maintained at a temperature of 180° C. and a pressure of 15 MPaG. The residence time was twenty minutes.

The condensate flowed upward from the bottom part of the condenser, and was collected from the top part by the down-flow-pipe 207, the pressure of the condensate raised by ejector 227 and transferred to the synthesis column 217.

An unabsorbed mixed gas containing 30.59 tons per day of ammonia, 49.45 tons per day of carbon dioxide and 3.88 tons per day of water was discharged from pipe 215 of the scrubbing portion J at the top of the condenser 216, and ammonia and carbon dioxide were subsequently recovered.

In the process and apparatus of Comparative Example 1, the load on the stripper is increased (compared to the process and apparatus of Example 1) due to a decrease in the rate of urea synthesis, and an increase in the amount of remaining unreacted ammonia and carbon dioxide in the urea solution obtained from the stripper. The amount of gas discharged from the scrubbing portion of the condensation column also increased.

COMPARATIVE EXAMPLE 2

Figure 5:
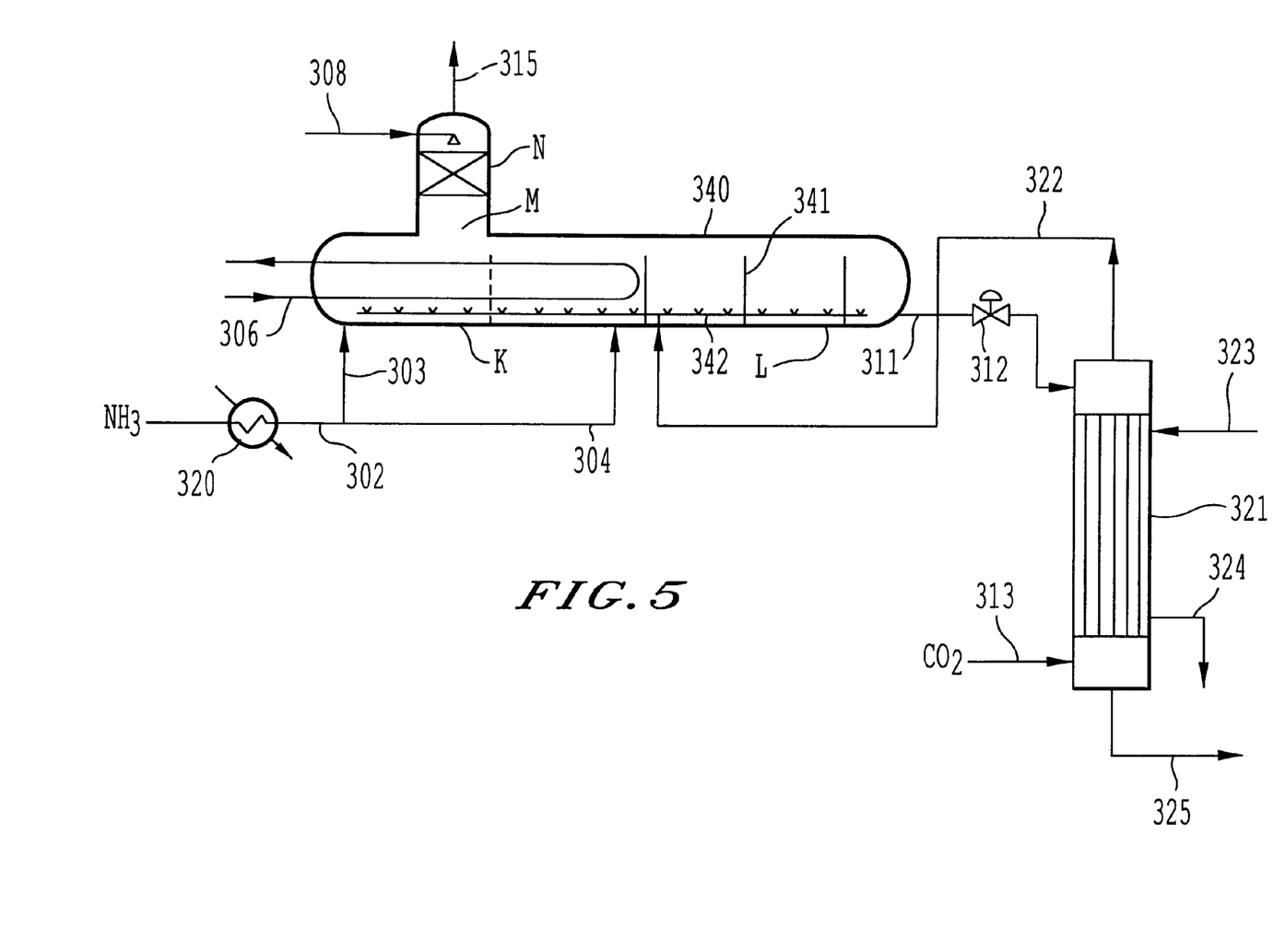
FIG. 5 is a diagram illustrating the process of Comparative Example 2.

An example of the production of 1725 tons per day of urea using horizontal condensation and synthesis equipment according to FIG. 5 is presented below for comparison with Example 1.

Cooling pipes were provided between one end and the middle part of the horizontal condensation and synthesis equipment 340, to provide a condensation portion K, and the scrubbing portion N for absorbing uncondensed gas was provided above the condensing portion K. In addition, a baffle plate 341 was placed in the horizontal condensation and synthesis equipment 340.

25.48 tons per day of liquid ammonia were introduced in the area near the inlet of the cooling pipe 306 in the condensation portion K of the horizontal condensation and synthesis equipment 340 through the lines 302 and 303, and 950.13 tons per day of liquid ammonia feedstock preheated to 75° C. by the pre-heater 320 were introduced into the boundary area between the condensation portion K and the synthesis portion L via pipe 304. Also, a recovered solution containing 5.23 tons per day of urea, 470.66 tons per day of carbon dioxide, 527.88 tons per day of carbon dioxide and 342.52 tons per day of water, obtained by separating/recovering the unreacted ammonia and carbon dioxide contained in the urea solution transferred from the stripper, was supplied to the top part of the above described scrubbing portion N via pipe 308 to absorb ammonia and carbon dioxide in the uncondensed gas. The absorbing liquid was then allowed to flow down to the cooling portion of the horizontal condensation and synthesis equipment 340. A mixed gas containing of 67.64 tons per day of ammonia, 28.02 tons per day of carbon dioxide and 5.94 tons per day of water was discharged through line 315 from the top part of the scrubbing portion N, and ammonia and carbon dioxide were subsequently recovered. The pressure of the horizontal condensation and synthesis equipment 340 was maintained at 15 MPaG, and the temperature of the condensing portion was maintained at 180° C. The condensate obtained in the cooling portion entered the synthesis portion L (the portion extending from the middle part to the outlet of the urea synthesis solution) of the horizontal condensation and synthesis equipment 340, where ammonium carbamate was produced from the liquid ammonia introduced via pipe 304, the mixed gas (described later) introduced from the stripper 321 and the uncondensed ammonia and carbon dioxide. The heat of reaction maintained the temperature of the synthesis portion L at 185° C. The residence time in the horizontal condensation and synthesis equipment 340 was forty minutes.

The urea synthesis solution containing 1853.90 tons per day of urea, 1956.40 tons per day of ammonia, 798.37 tons per day of carbon dioxide, 1052.96 tons per day of water and 4.31 tons per day of biuret, obtained from the horizontal condensation and synthesis equipment 340, was introduced into the stripper 321 via pipe 311 and control valve 312, and was contacted with 1211.58 tons per day of carbon dioxide introduced via pipe 313. The mixed gas containing 1628.42 tons per day of ammonia, 1656.91 tons per day of carbon dioxide and 160.29 tons per day of water was transferred from the top part of the stripper 321 through pipe 322 and a gas dispersion unit 342 into the horizontal condensation and synthesis equipment 340.

A urea solution containing 1764.23 tons per day of urea, 377.38 tons per day of ammonia, 416.24 tons per day of carbon dioxide, 866.79 tons per day of water and 7.24 tons per day of biuret was removed from the bottom part of the stripper 321 through pipe 325, and unreacted ammonia and carbon dioxide therein were separated/recovered to provide 1725 tons per day of urea.

In the process and apparatus of Comparative Example 2, the load on the stripper increased (compared to the process and apparatus of Example 1) due to a decrease in the rate of urea synthesis, and because the amount of ammonia and carbon dioxide in the urea solution also increased, the load on the low pressure decomposition and recovering steps increased. The amount of gas discharged from the scrubbing portion of the condensation and synthesis column also increased.

By using a vertical condensation and synthesis column with the functions of a vertical condenser and a synthesis column combined together, the following advantages can be provided by the processes and apparati of the present invention.

First, the amount of equipment is reduced, thus simplifying the placement and operation of the apparati of the present invention.

Second, since it is not necessary to supply carbon dioxide to the vertical condensation and synthesis column, the full amount of carbon dioxide can be supplied to the stripper, compared to conventional processes in which the condenser is separated from the synthesis column. Thus, the rate of stripping increases, resulting in reduction in the amount of ammonia and carbon dioxide in the urea solution obtained from the bottom part of the stripper As a result, the amount of unreacted ammonia and carbon dioxide that must be recovered at low pressure is reduced, and the H/C in the vertical condensation and synthesis column is thus decreased, resulting in an increase in the rate of urea synthesis.

Third, since the capacity coefficient of liquid phase ($K_L a$) is about twice as large as if a horizontal condensation and synthesis column, the rate of synthesis is increased. Also, the amount of gas discharged from the scrubber in the top part of the vertical condensation and synthesis column is reduced.

The priority document of the present application, Japanese patent application 202,482/2000 filed Jul. 4, 2000, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A urea synthesis process comprising:

reacting ammonia and carbon dioxide in a vertical condensation and synthesis zone which comprises a condensation portion extending from the bottom to the middle portion of the vertical condensation and synthesis zone, and a synthesis portion extending from the middle portion to the liquid surface of the top portion of the vertical condensation and synthesis zone, thereby providing a urea synthesis solution comprising urea, unreacted ammonia, unreacted carbon dioxide and water;

transferring the urea synthesis solution from a top portion of the vertical condensation and synthesis zone to a top portion of a stripping zone;

introducing carbon dioxide into a bottom portion of the stripping zone;

contacting the urea synthesis solution with the carbon dioxide in the stripping zone, thereby separating the unreacted ammonia and the unreacted carbon dioxide from the urea to provide a mixed gas comprising ammonia, carbon dioxide and water;

introducing the mixed gas into a bottom portion of the vertical condensation and synthesis zone;

introducing liquid ammonia into a bottom portion and a middle portion of the vertical condensation and synthesis zone;

contacting and cooling the mixed gas and liquid ammonia in the vertical condensation and synthesis zone, thereby condensing a portion of the mixed gas and producing urea;

absorbing the uncondensed portion of the mixed gas in an absorbing medium; and transferring at least a portion of the absorbing medium in which the uncondensed portion of the mixed gas is absorbed to a bottom portion of the vertical condensation and synthesis zone.

2. The urea synthesis process of claim 1, wherein the stripping zone has a pressure which is substantially equal to the urea synthesis pressure.

3. The urea synthesis process of claim 1, wherein the urea synthesis solution is transferred to the stripping zone by gravity.

4. The urea synthesis process of claim 1, wherein the stripping zone has a pressure which is equal to or slightly lower than the urea synthesis pressure.

5. The urea synthesis process of claim 1, wherein the pressure of the mixed gas transferred to the vertical condensation and synthesis zone is raised by 0.05 to 5 MPa.

6. The urea synthesis process of claim 5, wherein the stripping zone has a pressure which is equal to or slightly lower than the urea synthesis pressure.

7. The urea synthesis process of claim 5, wherein the stripping zone has a pressure which is substantially equal to the urea synthesis pressure.

8. The urea synthesis process of claim 1, further comprising discharging from the stripping zone the urea synthesis solution from which unreacted ammonia and carbon dioxide has been separated and further treating it to provide urea.

9. The urea synthesis process of claim 1, wherein the vertical condensation and synthesis zone comprises a lower portion extending from the bottom to the middle portion of the vertical condensation and synthesis zone, and the liquid in the lower portion is maintained at a temperature of 165 to 190° C.

10. The urea synthesis process of claim 9, wherein the liquid in the lower portion has a mole ratio of ammonia to carbon dioxide of 2.5 to 4.5.

11. The urea synthesis process of claim 9, wherein the liquid in the lower portion has a mole ratio of water to carbon dioxide of 1.0 or smaller.

12. The urea synthesis process of claim 9, wherein the liquid above the lower portion is maintained at a temperature of 170 to 200° C.

13. The urea synthesis process of claim 9, wherein the liquid above the lower portion has a mole ratio of ammonia to carbon dioxide of 3.5 to 5.0.

14. The urea synthesis process of claim 9, wherein the liquid above the lower portion has a mole ratio of water to carbon dioxide of 1.0 or smaller.

15. The urea synthesis process of claim 1, wherein the pressure in the vertical condensation and synthesis zone is in the range of 13 to 25 MPaG.

16. The urea synthesis process of claim 1, wherein the residence time in the vertical condensation and synthesis zone is 20 to 70 minutes.

* * * * *